United States Patent [19]
Koyama et al.

[11] Patent Number: 4,839,378
[45] Date of Patent: Jun. 13, 1989

[54] FLUOROPHTHALIMIDES AND AGRICULTURAL AND HORTICULTURAL FUNGICIDES CONTAINING THEM

[75] Inventors: Masao Koyama; Michiaki Iwata; Kunihiko Kurihara; Masaji Sezaki, all of Yokohama, Japan

[73] Assignee: Meiji Seika Kabushiki Kaisha, Tokyo, Japan

[21] Appl. No.: 43,330

[22] Filed: Apr. 28, 1987

[30] Foreign Application Priority Data

Apr. 30, 1986 [JP] Japan .................. 61-100541

[51] Int. Cl.$^4$ .................. A01N 37/32; C07D 209/48
[52] U.S. Cl. .................. 514/417; 548/476
[58] Field of Search .................. 548/476; 514/417

[56] References Cited

U.S. PATENT DOCUMENTS 2,657,169 10/1953 Ligett et al. .................. 514/417
3,922,284 11/1975 Heath et al. .................. 548/476

FOREIGN PATENT DOCUMENTS 054924 5/1976 Japan .

OTHER PUBLICATIONS

Fieser, et al., "Reagents for Organic Synthesis", John Wiley & Sons, Inc., 1967, pp. 934–935.
Fieser, et al., "Reagents for Organic Synthesis", vol. 5, John Wiley & Sons, New York, 1975, p. 556.

*Primary Examiner*—Donald G. Daus
*Assistant Examiner*—Diana G. Rivers
*Attorney, Agent, or Firm*—Emmanuel J. Lobato; Robert E. Burns

[57] ABSTRACT

Fluorophthalimide compounds represented by the following general formula (I):

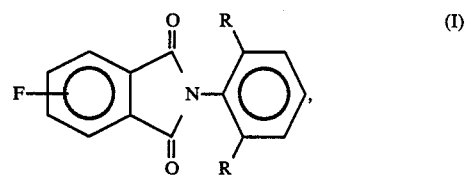

wherein R each stands for an ethyl group or an isopropyl group, are effective for controlling diseases of agricultural plants, especially diseases caused by microorganisms belonging to the genus Rhizoctonia, represented by sheath blight of rice plants, and diseases caused by Basidomycetes.

7 Claims, No Drawings

FLUOROPHTHALIMIDES AND AGRICULTURAL AND HORTICULTURAL FUNGICIDES CONTAINING THEM

BACKGROUND OF THE INVENTION

1. Field of the Invention

The present invention relates to a novel fluorophthalimide having an antimicrobial activity and also to an agricultural and horticultural fungicide comprising said fluorophthalimide as the active ingredient. It is an object of the present invention to provide a substance effective for controlling diseases of agricultural plants, especially diseases caused by microorganisms belonging to the genus Rhizoctonia, represented by sheath blight of rice plants, and diseases caused by Basidiomycetes.

2 Description of the Prior Art

It is known that phthalimides, especially N-(2'-6'-diethylphenyl)phthalimide and N-(2',6'-diisopropylphenyl)phthalimide, and agricultural preparations comprising the phthalimide as the active ingredient are effective for controlling sheath blight in rice plants (Japanese Patent Application Laid-Open Specifications No. 25736/75 and No. 30868/75).

However, it cannot be deemed that these phthalimides are prominently superior to antibiotic substances such as Validamycin and synthetic compounds such as N-(3'-isopropoxy)-2-methylbenzamido(Mepronyl). Accordingly, in order to provide a sheath blight-controlling agent having a higher practical utility, it has been desirable that some effective formulation of the fungicidal preparation be devised or such a phthalimide be chemically converted to a derivative having an enhanced antimicrobial activity.

SUMMARY OF THE INVENTION

It is a primary object of the present invention to solve the above mentioned problem.

According to the present invention, this object can be attained by providing a compound formed by introducing fluorine into a known phthalimide as described above.

More specifically, in accordance with the present invention in one aspect thereof, there is provided a fluorophthalimide compound represented by the following general formula (I):

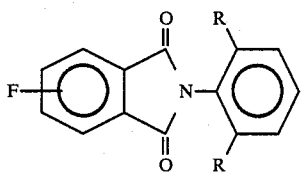

wherein R each stands for an ethyl group or an isopropyl group.

In accordance with another aspect of the present invention, there is provided a process for the preparation of fluorophthalimide compounds represented by the following general formula (I):

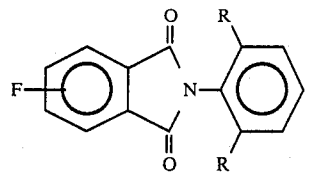

wherein R each stands for an ethyl group or an isopropyl group, which comprises reacting a phthalimide compound represented by the following general formula (IV):

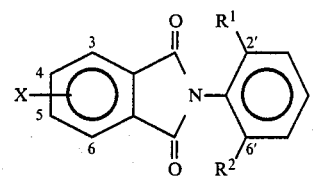

wherein R each is as defined above and Y stands for an electron-attracting group, with a fluorine ion supply source compound.

In accordance with still another aspect of the present invention, there is provided an agricultural and horticultural fungicide which comprises as an active ingredient a fluorophthalimide represented by the general formula (I):

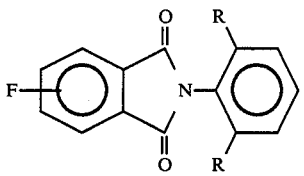

wherein R each stands for an ethyl group or an isopropyl group.

The fluorophthalimide compound represented by the general formula (I) is synthesized by fluorination of a corresponding phthalimide compound, which fluorination can, contrary to conventional fluorination which is generally difficult, be accomplished very easily as described in detail hereinafter.

This phthalimide compound has a much higher activity in inhibiting the growth of microorganisms causing sheath blight in rice plants than the known corresponding phthalimide compound having no fluorine, and furthermore, this fluorophthalimide compound exhibits a strong growth-inhibiting action with respect to other agricultural and horticultural microorganisms.

This fluorophthalimide compound is chemically stable and can be stored for a long time. By dint of this good chemical stability as well as the above-mentioned strong growth-inhibiting activity with respect to agricultural and horitcultural microorganisms, an agricultural and horticultural fungicide comprising this fluorophthalimide compound as the active ingredient shows a very high practical utility.

DETAILED DESCRIPTION

Fluorophthalimide Compound

Design of Chemical Structure

We carried out fundamental research on the interrelation between the chemical structure and the activity of controlling sheath blight in rice plants with respect to the above mentioned known phthalimides and related compounds thereof. As a result, it was found that in an N-(2',6'-dialkylphenyl)phthalimide represented by the following general formula (II):

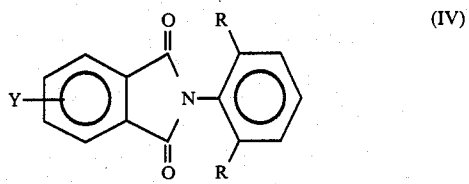

wherein X stands for a hydrogen atom, a nitro group, an alkoxycarbonyl group, an acylamino group or other common substituent, and $R^1$ and $R^2$ stand for a hydrogen atom or a lower alkyl group, there is a definite relation between this chemical structure and the activity of controlling sheath blight in rice plants. More specifically, a phthalimide (II) having a substituent other than hydrogen at the 3-position has generally a low activity. the effect of the substituent at the 4-position is influenced by the steric hindrance, and it is considered that a smaller substituent is preferable. In phthalimides (II), it is indispensable that each of the substituents at the 2'-and 6'-positions can be an alkyl group, and it is presumed that it is necessary that one of these substituents should have a size larger than that of the ethyl group. In view of the foregoing, it is concluded that among phthalimides represented by the general formula (II), the substances expected to exert the greatest effect are substances having hydrogen atoms at the 3- and 4-positions and alkyl groups at the 2'- and 6'-positions, that is, known N-(2',6'-diethylphenyl)phthalimide and N-(2',6'-diisopropylphenyl)phthalimide.

In connection with fluorine derivatives of these compounds, the synthesis process has not been known, and it has not been known that these derivatives have an activity of controlling sheath blight in rice plants.

It is known that if a fluorine atom is introduced into a physiologically active substance, the fluorinated part is chemically or biologically stabilized, and that since the atomic radius of the fluorine atom is substantially equal to that of the hydrogen atom, occurrence of the steric hindrance is more controlled than in the case where another substituent is introduced. In some compounds, the physiological activity is increased by introduction of a fluorine atom.

According to the present invention, by selecting fluorine as X in the compound represented by the above mentioned general formula (II), the activity of controlling sheath blight in rice plants, inherently observed in the chemical structure represented by the general formula (II), is increased to the highest level.

This concept for the design of the chemical structure has now been perfected as an invention based on the development of a fluorination process that can be easily carried out and confirmation of an unexpectedly high activity of controlling sheath blight in rice plants.

Specific Examples of Compound

The fluorophthalimide compound according to the present invention is represented by the above mentioned formula (I).

In this formula (I), R each stands for an ethyl group or an isopropyl group, and in general, the two Rs are the same. The substitution position of fluorine is not critical.

Specific examples of the compounds are: N-(2',6'-diethylphenyl)-3-fluorophthalimide; N-(2',6'-diethylphenyl)-4-fluorophthalimide; N-(2',6'-diisopropylphenyl)-3-fluorophthalimide; and N-(2',6'-diixopropylphenyl)-4-fluorophthalimide.

Synthesis of Fluorophthalimide Compound

The compound of the general formula (I) can be easily synthesized according to the reaction represented by the following reaction formula:

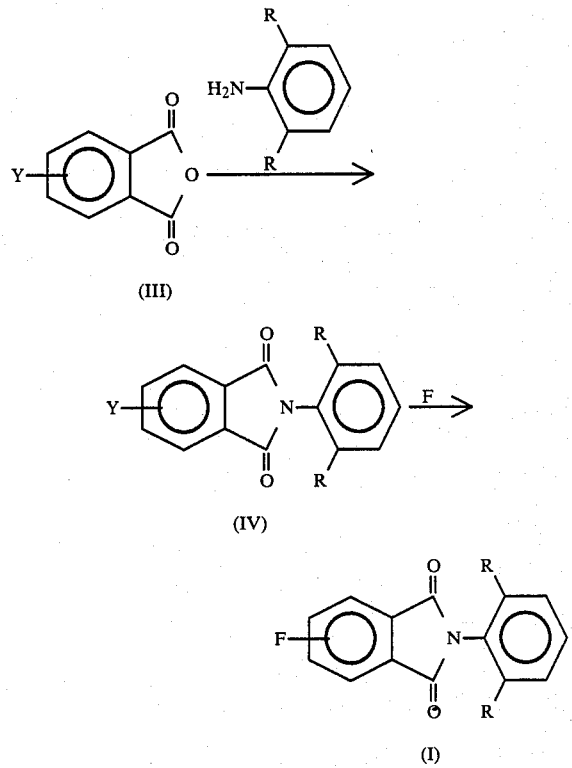

In the above reaction formula, R each stands for an ethyl group or an isopropyl groups, and X stands for an electron-attracting groups such as a nitro group, a chlorine atom or a bromine atom.

More specifically, this process comprises preparing a phthalimide (IV) from a phthalic anhydride derivative (III) having an electron-attracting group (Y) and a dialkylaniline and substituting the substituent Y of the phthalimide with a fluorine ion to produce a fluorophthalimide (I).

The first step of synthesizing the phthalimide (IV) in this synthesis process is a well-known process, and in this step, the phthalic anhydride derivative (III) and the alkylaniline are heated and reacted in an inert solvent such as acetic acid or in the absence of a solvent.

The fluorination reaction of the second step is characterized in that a special fluorinating agent need not be used, and the reaction is carried out in the liquid phase by using a hydrofluoric acid salt, which can be easily handled, such as potassium fluoride. This fluorination process has very high safety. More specifically, if a phthalimide (IV) having as a substituent an appropriate electron-attracting group (the definition and examples of the electron-attracting group are described in textbooks of organic electron theory) such as a nitro group or a halogen atom other than fluorine (for example, a chlorine atom or a bromine atom) is dissolved in a polar solvent such as dimethylsulfoxide or dimethylformamide, and the solution is mixed with an excessive amount, preferably 3 to 6 equivalents, of an alkali metal fluoride, preferably potassium fluoride, and heated at an appropriate temperature, preferably 80° to 130° C., the substitution reaction will be advanced. Isolation and purification of the fluorophthalimide produced from the reaction mixture can be accomplished by appropriately combining known methods such as solvent extraction, recrystallization and column chromatography.

Use of Fluorophthalimide Compound

Agricultural and Horticultural Fungicide

The fluorophthalimide compound (I) of the present invention is effective for controlling a variety of plant diseases caused by molds and is especially effective for controlling diseases caused by Rhizoctonia, such as sheath blight in rice plants, sheath blight in mat rush, foot rot or damping-off in vegetable seedlings and black scurf in potato, and diseases caused by Basidiomycetes such as those causing typhula snow blight, smut, rust and brown spot. Accordingly, the compound of the present invention can be used as a valuable agent for controlling these diseases.

The agricultural and horticultural fungicide of the present invention can take an optional form or application mode customarily adopted for agricultural and horitcultural chemicals, especially fungicides, except that the active ingredient is the above mentioned fluorophthalimide (I). More specifically, the fluorophthalimide (I) of the present invention is directly diluted with water, a powdery solid or other appropriate carrier. If necessary, an adjuvant such as a spreader is added to the dilution, and the resulting composition is used. Alternatively, the fluorophthalimide (I) is mixed with a liquid or solid carrier according to a method customarily adopted in the field of agricultural chemicals, and, if necessary, an adjuvant such as a wet spreader, a spreader, a dispersant, an emulsifier, a binder or a lubricant is added. The fluorophthalimide (I) is used in the form of a wettable powder, a liquid preparation, an emulsion, a dust, a granule or a fine granule.

As the liquid carrier to be used for such preparations of the fluorophthalimide (I), a liquid which can be a solvent for the fluorophthalimide (I) or a liquid which is capable of dispersing or dissolving the fluorophthalimide (I) therein with the aid of an adjuvant can be used. For example, aromatic hydrocarbons, aliphatic hydrocarbons, alcohols, esters, ketones and liquids having high polarity, such as dimethylformamide and dimethylsulfoxide can be used. As the solid carrier, powders of mineral substances such as clay, kaolin, talc, diatomaceous earth, bentonite, calcium carbonate and silica, gravel, wood flour, and powders and granules of organic substances can be used. As the adjuvant, nonionic, anionic, cationic and amphoteric surface active agents, lignin-sulfonic acid and its salts, gums, fatty acid salts and methyl cellulose pastes can be used.

The agricultural and horticultural fungicide of the present invention can be applied to stalks or leaves of plants, or it may be applied to the water surface or into water, or to the soil surface or into the soil. Moreover, the agricultural and horticultural fungicide of the present invention may be used in a state mixed with a compatible agricultural or horticultural chemical or fertilizer. Examples of the agricultural or horticultural chemical are fungicides, insecticides, herbicides and plant growth modifiers.

In the case where the agricultural and horticultural fungicide is used in the form of a liquid preparation, it is preferable that the concentration of the fluorophthalimide (I) in the liquid to be sprayed be in the range of 10 to 1,000 ppm (a concentrated spray liquid can be used in the case of spraying of a small amount of a concentrate or in case of spraying by an airplane). In the case of a dust, granule or fine granule, it is preferable that the content of the fluorophthalimide (I) be 0.1 to 50%.

The amount applied of the agricultural and horticultural fungicide of the present invention is changed according to the kind and degree of the disease to be controlled, the kind of the objective plant, the application mode and other factors, but, in the case of soil application, in general, a wettable powder (having an active ingredient content of 40%) is applied in an amount of 50 to 200 liters per 10 ares; a water-soluble powder (having an active ingredient content of 40%) is applied in an amount of 50 to 200 liters per 10 acres; a granule (having an active ingredient of 15%) is applied in an amount of 2 to 6 kg per 10 acres; and a dust (having an active ingredient of 3%) is applied in an amount of about 2 to about 6 kg per 10 acres.

EXPERIMENTAL EXAMPLES

The synthesis of the fluorophthalimide (I) of the present invention and formation of the fluorophthalimide into various preparations will now be described in detail by way of the following examples that by no means limit the scope of the invention. It must be noted that many changes and modifications not illustrated in the examples can be adopted.

EXAMPLE 1

Synthesis of N-(2',6'-diethylphenyl)-3-fluorophthalimide (Compound 1)

In 150 ml of dimethylsulfoxide was dissolved 16.2 g of N-(2',6'-diethylphenyl)-3-nitrophthalimide. 10 g of potassium fluoride was added to the solution, and the mixture was heated on an oil bath at 100° C. for 4 hours. The liquid reaction mixture was concentrated at 80° C. under reduced pressure. Then, 200 ml of ethyl acetate and 200 ml of water were added to the residue to extract the desired product. The ethyl acetate layer was separated, washed with water, dried and concentrated under reduced pressure to form a dark-red oil. Then, 50 ml of methanol was added to the oil; the mixture was cooled; impurities were removed by filtration; and the filtrate was concentrated and dried. The dark-red oil was adsorbed on 100 g of silica gel packed in a column. Elution was carried out with benzene, and the compound 1 was obtained as a first fraction. The fraction was collected and concentrated to obtain a colorless oil. When 20 ml of hexane was added to the oil, a crystal of the compound 1 was precipitated. The amount obtained of the crystal was 6.08 g, yield: 40.9%.

EI Mass: M/Z 297 (M+).

$^1$HNMR (CDCl$_3$), δ(ppm): 7.77–7.84 (m, 2H), 7.45–7.50 (m, 1H), 7.40 (t, 1H), 7.24 (d, 2H), 2.45 (q, 4H), 1.13 (t, 6H).

EXAMPLE 2

Synthesis of N-(2',6'-diethylphenyl)-4-fluorophthalimide (Compound 2)

In 40 ml of dimethylsulfoxide was dissolved 1.00 g of N-(2',6'-diethylphenyl)-4-nitropthalimide. 1.00 g of potassium fluoride was added to the solution, and the mixture was heated with stirring on an oil bath at 130° C. for 10 hours. The liquid reaction mixture was concentrated under reduced pressure at 80° C. The residue was extracted with ethyl acetate, and the extract was washed with water and dried. The ethyl acetate solution was concentrated, and the residue was purified by column chromatography by using 120 g of silica gel (solvent system: benzene/ethyl acetate, 100/0-90/10). The desired fluorine compound was obtained as a first fraction. The amount obtained of the objective compound was 444 mg, yield: 48.4%.

EI Mass: M/Z 297 (M+):

$^1$HNMR (CDCl$_3$), δ(ppm): 7.97 (dd, 1H), 7.64 (dd, 1H), 7.47 (m, 1H), 7.39 (t, 1H), 7.23 (d, 2H), 2.45 (q, 4H), 1.13 (t, 6H).

EXAMPLE 3

Synthesis of N-(2',6'-diisopropylphenyl)-3-fluorophthalimide (Compound 3)

In 300 ml of dimethylsulfoxide was dissolved 14.0 g of N-(2',6'-diisopropylphenyl)-3-nitrophthalimide, and 10.0 g of potassium fluoride was added to the solution. The mixture was heated on an oil bath at 100° C. for 3 hours. The liquid reaction mixture was concentrated under reduced pressure below 80° C., and the residue was extracted with ethyl acetate. The ethyl acetate solution was washed with water, dried and concentrated. Then, 20 ml of methanol was added to the residue, and the mixture was cooled and allowed to stand still. The compound 3 was precipitated in the form of colorless crystals. The amount obtained of the crude product was 10.1 g, yield: 77.6%. The crude crystals were recrystallized from methanol two times to obtain 4.5 g of pure crystals.

EI Mass: M/Z 325 (M+).

$^1$HNMR (CDCL$_3$), δ(ppm): 7.73–7.80 (m, 2H), 7.43–7.5 (m, 2H), 7.29 (d, 2H), 2.69 (m, 2H), 1,18 (d, 9H).

EXAMPLE 4

Synthesis of N-(2',6'-diisopropylphenyl)-4-fluorophthalimide (Compound 4)

In 30 ml of dimethylsulfoxide was dissolved 1.00 g of N-(2',6'-diisopropylphenyl)-4-nitrophthalimide. 0.8 g of potassium fluoride was added to the solution, and the mixture was stirred on an oil bath at 120° C. for 8 hours. The reaction mixture liquid was concentrated under reduced pressure below 80° C., and the residue was extracted with 50 ml of ethyl acetate. The extract was washed with water and dried, and the ethyl acetate layer was concentrated. When the residue was purified by column chromatography by using 100 g of silica gel (solvent system: benzene), the compound 4 was obtained as the first fraction. The amount obtained of the compound 4 was 473 mg, yield: 50.9%.

EI Mass: M/Z 325 (M+). $^1$HNMR (CDCl$_3$), δ(ppm): 7.98 (dd, 1H), 7.65 (dd, 1H), 7.48 (m, 1H), 7.47 (t, 1H), 7.27 (d, 2H), 2.69 (m, 2H), 1.18 (d, 9H).

Preparation Example 1

Wettable Powder

| Ingredients | Amount (parts by wt.) |
| --- | --- |
| Compound 1 | 40 |
| Clay | 10 |
| Diatomaceous earth | 45 |
| Lignin-sulfonic acid | 3 |
| Polyoxyethylene alkylaryl ether | 2 |

The above ingredients are homogeneously pulverized and mixed to obtain a wettable powder having an effective ingredient content of 40%.

Preparation Example 2 Granule

| Ingredients | Amount (parts by wt.) |
| --- | --- |
| Compound 2 | 15 |
| Clay | 82 |
| Carboxymethyl cellulose | 3 |

The above ingredients are mixed, and an appropriate amount of water is added to the mixture. The mixture is kneaded, granulated and dried to obtain a granule having an effective ingredient content of 15%.

Preparation Example 3

Dust

| Ingredients | Amount (parts by wt.) |
| --- | --- |
| Compound 3 | 1 |
| Calcium stearate | 3 |
| Anhydrous silicic acid powder | 1 |
| Clay | 48 |
| Talc | 47 |

The above ingredients are homogeneously pulverized and mixed to obtain a dust having an effective ingredient content of 3%.

Preparation Example 4

Emulsifiable Liquid

| Ingredients | Amount (parts by wt.) |
| --- | --- |
| Compound 4 | 20 |
| cyclohexanone | 20 |
| Xylene | 45 |
| Polyoxyethylene alkylphenyl ether | 12 |
| Calcium alkylbenzenesulfonate | 3 |

The above ingredients are homogeneously mixed and dissolved to obtain an emulsifiable liquid having an active ingredient content of 20%.

Preparation Example 5

Flowable Liquid

| Ingredients | Amount (parts by wt.) |
| --- | --- |
| Compound 3 | 40 |
| Machine oil | 52 |
| Polyoxyethylene alkylphenyl ether | 5 |
| Calcium alkylbenzenesulfonate | 3 |

The above ingredients are homogeneously mixed and dissolved to obtain a flowable liquid having an active ingredient content of 40%.

Test 1

Antimicrobial Test to Sheath Blight in Rice Plants

The degree of the growth of hyphae of *Rhizoctonia solani* causing sheath blight in rice plants on an agar plate was examined. More specifically, the test compound was incorporated into a Czapek agarculture medium to form a dilution system, and the culture medium was cast in a Petri dish and solidified to form an agar plate. The agar plate was inoculated with the microorganism causing sheath blight in rice plants and culturing was conducted at 25° C. for 48 hours. The degree of growth of hyphae was examined. The results thus obtained are shown in Table 1. The compounds of the present invention showed a strong antimicrobial activity with respect to the microorganism causing sheath blight in rice plants.

TABLE 1

Antimicrobial Test to Sheath Blight in Rice Plants

| Chemical Tested | Concentration (ppm) Degree of Growth of Hyphae | | | | |
|---|---|---|---|---|---|
| | 10 | 5 | 1.0 | 0.5 | 0.1 |
| Compound 1 | — | — | — | ± | + |
| Compound 2 | — | — | ± | ± | + |
| Compound 3 | — | — | — | — | ± |
| Compound 4 | — | — | — | ± | ± |
| N—(2',6'-diethylpheny)-phthalimide | ± | ± | ± | ++ | ++ |
| N—(2',6'-diisopropylphenyl)phthalimide | — | ± | ± | + | ++ |

Note
++: normal growth,
+: control of growth,
±: strong control of growth,
—: complete inhibition of growth

Test 2 Test of Control of Sheath Blight in Rice Plants

Spraying Treatment of Leaves and Stalks

The wettable powder obtained according to the method described in Preparation Example 1 was formed into a spraying liquid having a specific concentration, and the spraying liquid was sprayed at a rate of 70 ml per 3 pots on paddy rice (variety: jukkoku) of the seedling stage cultivated in a Wagner pot having an area of 1/5000 are. After air-drying, the rice plants were inoculated by culturing the microorganism causing sheath blight therein in a peptone-added potato bouillon agar culture medium for 48 hours according to the plate culturing method, punching the plate into a disc having a diameter of 0.5 cm by a cork borer and inserting the microorganism-containing agar piece into the center of the stalk at a height of 15 cm from the ground surface.

After the inoculation, in order to promote intrusion and development of the microorganism causing sheath blight, each pot was covered with a vinyl resin cylinder and placed in a glass green house maintained at 30° C. at daytime and at 24° C. at night to cause the outbreak of the disease. When 10 days had passed from the time of the inoculation treatment, the length of the disease stigma was measured and the control value was calculated according to the following equation:

$$\text{Control value} = \left(1 - \frac{\text{Average disease stigma length in treated section}}{\text{Average disease stigma length in untreated section}}\right) \times 100$$

Furthermore, the state of the pytotoxicity was simultaneously checked by naked eye observation.

The results obtained are shown in Table 2. The compounds of the present invention showed a high control effect with respect to the disease causing sheath blight in rice plants by the spraying treatment of stalks and leaves.

TABLE 2

Test of Control of Sheath Blight in Rice Plants (Scattering Treatment of Stalks and Leaves)

| Chemical Tested | Concentration (ppm) | Control Value (%) | Phytotoxicity |
|---|---|---|---|
| Compound 1 | 200 | 100 | — |
| | 100 | 99 | — |
| | 50 | 96 | — |
| Compound 2 | 200 | 99 | — |
| | 100 | 95 | — |
| | 50 | 89 | — |
| Compound 3 | 200 | 100 | — |
| | 100 | 100 | — |
| | 50 | 97 | — |
| Compound 4 | 200 | 99 | — |
| | 100 | 96 | — |
| | 50 | 93 | — |
| N—(2',6'-diethylphenyl)-phthalimide | 200 | 99 | — |
| | 100 | 94 | — |
| | 50 | 88 | — |
| N—(2',6'-diisopropylphenyl)-phthalimide | 200 | 99 | — |
| | 100 | 96 | — |
| | 50 | 90 | — |
| N—(3'-isopropyloxy)-2-methylbenzamide wettable powder (commercially available comparative chemical) | 200 | 96 | — |
| | 100 | 94 | — |
| | 50 | 92 | — |
| Untreated | 0 | 0 | — |

Note
—: no phytotoxicity

Test 3

Test of Control of Sheath Blight in Rice Plants

Application to Water Surface

The granule prepared in Preparation Example 2 was sprayed at a rate of 3 kg/10 ares among stalks of paddy rice of the seedling stage as treated in Test 2. After passage of 5 days, the plant was inoculated with the microorganism causing sheath blight in rice plants in the same manner as described in Test 2.

The test results are shown in Table 3. The compounds of the present invention showed a high control effect with respect to sheath blight in rice plants also by the application to the water surface.

TABLE 3

Test of Control of Sheath Blight in Rice Plants (Application to Water Surface)

| Chemical Tested | Amount (Kg/10 a) | Control value (%) | Phytotoxicity |
|---|---|---|---|
| Compound 1 | 3 | 88 | — |
| Compound 2 | 3 | 86 | — |
| Compound 3 | 3 | 92 | — |
| Compound 4 | 3 | 89 | — |

TABLE 3-continued

Test of Control of Sheath Blight in Rice Plants
(Application to Water Surface)

| Chemical Tested | Amount (Kg/10 a) | Control value (%) | Phytotoxicity |
|---|---|---|---|
| Untreated | 0 | 0 | — |

Note
—: no phytotoxicity

Test 4

Test of Control of Damping-off in Cucumber Seedlings

The microorganism causing damping-off in cucumber was cultured on a potato bouillon agar culture medium, and the culture medium was mixed and pulverized with rice bran in an amount 3 times the amount of the culture medium to form an inoculation source. The inoculation source was homogeneously mixed with the sterilized field soil, and the mixture was packed in a Wagner pot having an area of 1/5000 are. The pot was placed in a thermostat chamber at 28° C. for 48 hours. An irrigation liquid containing the wettable powder prepared in Preparation Example 1 at a specific concentration was uniformly applied to the ground surface at a rate of 100 ml per pot by a pipette. After one day, sprouting seeds of cucumber (variety: shiyo) were scattered at a rate of 20 seeds per pot. In order to promote intrusion and development of the inoculated microorganism, the pot was plated in a glass green house maintained at 28° to 30° C., and the soil in the pot was kept relatively dry to cause the outbreak of the disease. The test was carried out according to the 3 pots-1 section system. After the passage of 3 weeks, the numbers of sprouts and healthy seedlings were checked, and the sprouting ratio and healthy seedling ratio to the scattered seeds were calculated.

The results obtained are shown in Table 4. The compounds of the present invention showed a high control effect with respect to damping-off in cucumber.

TABLE 4

Test of Control of Damping-off in Cucumber

| Chemical Tested | Concentration (ppm) | Sprout Ratio (%) | Healthy Seedling Ratio (%) | Phytotoxicity |
|---|---|---|---|---|
| Compound 1 | 200 | 100 | 100 | — |
|  | 100 | 100 | 93 | — |
| Compound 2 | 200 | 100 | 97 | — |
|  | 100 | 98 | 92 | — |
| Compound 3 | 200 | 100 | 100 | — |
|  | 100 | 100 | 100 | — |
| Compound 4 | 200 | 100 | 98 | — |
|  | 100 | 98 | 93 | — |
| N—(2',6'-dimethylphenyl)-phthalimide | 200 | 100 | 95 | — |
|  | 100 | 97 | 85 | — |
| N—(2',6'-diisopropylphenyl)-phthalimide | 200 | 100 | 95 | — |
|  | 100 | 98 | 87 | — |
| pentachloronitrobenzene wettable powder (commercially available comparative chemical) | 200 | 93 | 82 | — |
|  | 100 | 87 | 70 | — |
| Untreated | 0 | 47 | 3 | — |

Note
—: no phytotoxicity

What is claimed is:

1. A fluorophthalimide compound represented by the following formula (I):

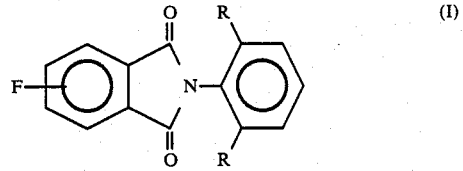

wherein R each stands for an ethyl group or an isopropyl group.

2. A compound as set forth in claim 1, which is N-(2',6'-diethylphenyl)-3-fluorophthalimide.

3. A compound as set forth in claim 1, which is N-(2',6'-diisopropylphenyl)-3-fluorophthalamide.

4. A compound as set forth in claim 1, which is N-(2',6'-diisopropylphenyl)-3-fluorophthalimide.

5. A compound as set forth in claim 1, which is N-(2',6'-diisopropylphenyl)-4-fluorophthalimide.

6. An agricultural and horticultural fungicide which comprises as an active ingredient a fluorophthalimide represented by the formula (I):

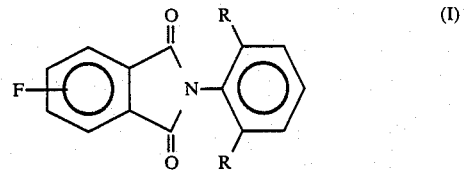

wherein R each stands for an ethyl group or an isopropyl group.

7. An agricultural and horticultural fungicide as set forth in claim 6, wherein the compound represented by the general formula (I) is selected from the group consisting of N-(2',6'-diethylphenyl)-3-fluorophthalimide, N-(2',6'-diethylphenyl)-4-fluorophthalimide, N-(2',6'-diisopropylphenyl)-3-fluorophthalimide and N-(2',6'-diisopropylphenyl)-4-fluorophthalimide.

* * * * *